(12) United States Patent
Young et al.

(10) Patent No.: US 11,583,997 B2
(45) Date of Patent: *Feb. 21, 2023

(54) AUTONOMOUS ROBOT

(71) Applicant: Sony Corporation, Tokyo (JP)

(72) Inventors: David Young, San Diego, CA (US);
Lindsay Miller, San Diego, CA (US);
Lobrenzo Wingo, San Diego, CA (US);
Marvin DeMerchant, San Diego, CA (US)

(73) Assignee: Sony Group Corporation, Tokyo (JP)

( * ) Notice: Subject to any disclaimer, the term of this patent is extended or adjusted under 35 U.S.C. 154(b) by 687 days.

This patent is subject to a terminal disclaimer.

(21) Appl. No.: 16/137,143

(22) Filed: Sep. 20, 2018

(65) Prior Publication Data
US 2020/0094397 A1 Mar. 26, 2020

(51) Int. Cl.
*G06F 17/00* (2019.01)
*B25J 9/00* (2006.01)
(Continued)

(52) U.S. Cl.
CPC .......... *B25J 9/0003* (2013.01); *B25J 9/1697* (2013.01); *B25J 11/008* (2013.01); *B25J 13/003* (2013.01);
(Continued)

(58) Field of Classification Search
CPC ........ B25J 9/0003; B25J 9/1697; B25J 13/08; B25J 13/003; B25J 11/008; G05B 15/02; G06K 9/3233; G05D 1/0246; G05D 2201/0209; G06F 3/011; A61B 5/0205; A61B 5/00; G08B 25/009; G08B 21/0476;
(Continued)

(56) References Cited

U.S. PATENT DOCUMENTS 9,367,811 B2 * 6/2016 Ramachandran ...... G06V 10/96
9,767,360 B2 * 9/2017 Cho ........................ G06V 10/44
(Continued)

FOREIGN PATENT DOCUMENTS

FR 2966763 A1 * 5/2012 ............ B25J 9/0003
WO WO-2017175707 A1 * 10/2017 ............... G06T 7/20

OTHER PUBLICATIONS http://www.bluefrogrobotics.com/en/buddy/ BUDDY—The Companion Robot Buddy the First Companion Robot 5 pages.
(Continued)

*Primary Examiner* — Ronnie M Mancho
(74) *Attorney, Agent, or Firm* — Trellis IP Law Group, PC (57) ABSTRACT

A robot in a location interacts with a user. The robot includes a camera, an image recognition processor, a microphone and a loudspeaker, a voice assistant, and a wireless transceiver. The robot moves around and creates a model of the location, and recognizes changes. It recognizes objects of interest, beings, and situations. The robot monitors the user and recognizes body language and gesture commands, as well as voice commands. The robot communicates with the user, the TV, and other devices. It may include environment sensors and health status sensors. It acts as a user companion by answering queries, executing commands, and issuing reminders. It may monitor to determine if the user is well. The robot may monitor objects of interest, their placement and their status. When necessary, it communicates with the user.

17 Claims, 9 Drawing Sheets (51) Int. Cl.
 B25J 9/16 (2006.01)
 B25J 13/08 (2006.01)
 B25J 13/00 (2006.01)
 B25J 11/00 (2006.01)
 G05D 1/02 (2020.01)
 G05B 15/02 (2006.01)
 G06V 10/25 (2022.01)
 G06F 3/01 (2006.01)

(52) U.S. Cl.
 CPC ............. *B25J 13/08* (2013.01); *G05B 15/02* (2013.01); *G05D 1/0246* (2013.01); *G06V 10/25* (2022.01); *G05D 2201/0209* (2013.01); *G06F 3/011* (2013.01)

(58) Field of Classification Search
 CPC ........ G08B 17/10; G08B 25/10; G08B 25/08; G08B 25/14
 USPC .......................................................... 700/257
 See application file for complete search history.

(56) References Cited

U.S. PATENT DOCUMENTS

| 10,108,850 | B1* | 10/2018 | Das | ..................... G06K 9/00885 |
| 10,635,902 | B2* | 4/2020 | Lee | ....................... B64C 39/024 |
| 2007/0192910 | A1* | 8/2007 | Vu | ........................... B25J 19/06 |
| | | | | 700/245 |
| 2007/0198128 | A1 | 8/2007 | Ziegler et al. | |
| 2009/0055019 | A1 | 5/2009 | Stiehl et al. | |
| 2013/0304257 | A1* | 11/2013 | Wang | ..................... B25J 9/1697 |
| | | | | 700/249 |
| 2017/0293297 | A1* | 10/2017 | Kim | ....................... G06V 20/17 |
| 2017/0351900 | A1* | 12/2017 | Lee | ...................... G06V 40/166 |
| 2017/0374397 | A1* | 12/2017 | Rylskiy | ................. H04N 21/84 |
| 2019/0028903 | A1* | 1/2019 | Carpenter | ............. G08G 5/006 |
| 2019/0102667 | A1* | 4/2019 | Bashkirov | .............. G06V 20/20 |
| 2019/0130180 | A1* | 5/2019 | Shiraishi | ................... G06T 7/20 |
| 2019/0394057 | A1* | 12/2019 | Bujnowski | ............. G06Q 10/10 |
| 2020/0094398 | A1* | 3/2020 | Young | .................... B25J 11/008 |
| 2020/0262067 | A1* | 8/2020 | Bryner | ................. G01N 29/225 |
| 2021/0316452 | A1* | 10/2021 | Ozaki | .................. B25J 11/0005 |
| 2022/0331945 | A1* | 10/2022 | Bryner | ................... B25J 19/021 |

OTHER PUBLICATIONS https://news.brown.edu/ARTICLES/2017/11/ARIES Brown; Hasbro team to design smart robotic companions to assist seniors https://news.brown.edu/articles/2017/11/aries; Kevin Stacey; Nov. 1, 2017.
https://www.allhomerobotics.com/the-full-aido-robot-review-youll-love/ Check This Out: The Full Aido Robot Review You'll Love https://www.allhomerobotics.com/the-full-aido-robot-review-youll-love/; Patrick Sinclair.

* cited by examiner

| Environment sensors | Health status sensors |
|---|---|
| Ambient temperature | Heart rate |
| Infrared light | Body temperature |
| Ultraviolet light | Blood pressure |
| Electromagnetic waves | Blood composition |
| Smoke | ... |
| Carbon monoxide | |
| Humidity | |
| Location | |
| Movement | |
| ... | |

200

220

Actuators

Position

Shape

Attitude

Sound

Image

AUTONOMOUS ROBOT

CROSS REFERENCES TO RELATED APPLICATIONS

This application is related to U.S. patent application Ser. No. 16/102,639, entitled "Method and Apparatus for Assisting a TV User", and client reference no. 201705845.01, filed on Aug. 13, 2018, which is hereby incorporated by reference, as if set forth in full in this specification.

This application is further related to U.S. patent application Ser. No. 16/137,153, entitled "A Situation-Aware Robot", and client reference no. 201805934.01, filed concurrently herewith, which is hereby incorporated by reference, as if set forth in full in this specification.

BACKGROUND

The present invention is in the field of smart homes, and more particularly in the field of robotics and voice assistants.

There is a need to provide useful, robust and automated, services to a person. Many current services are tied to television (TV) and, therefore, only provided or useful if a user or an object of interest is within view of stationary cameras and/or agents embedded in or stored on a TV. Other current services are tied to a voice assistant such as Alexa, Google Assistant, and Siri. Some voice assistants are stationary, others are provided in a handheld device (usually a smartphone). Again, usage is restricted when the user is not near the stationary voice assistant or is not carrying a handheld voice assistant. Services may further be limited to appliances and items that are capable of communication, for instance over the internet, a wireless network, or a personal network. A user may be out of range of a TV or voice assistant when in need, or an object of interest may be out of range of those agents.

One example of an object of interest is an appliance such as a washing machine. Monitoring appliances can be impossible or very difficult because of the above described conditions. Interfacing the TV with the appliance electronically may be difficult when the appliance is not communication-enabled. Thus, while at home watching TV or performing other activities, people tend to forget about appliances that are performing household tasks. Sometimes an appliance can finish a task and the user wants to know when it is done. Other times an appliance may have a problem that requires the user's immediate attention. The user may not be able to hear audible alarms or beeps from the appliance when he or she is in another room.

A further problem is that currently available devices and services offer their users inadequate help. For example, a user who comes home from work may have a pattern of turning on a TV or audio system and all connected components. Once the components are on, the user may need to press multiple buttons on multiple remote controls to find desired content or to surf to a channel that may offer such content. Currently there are solutions for one-button push solutions to load specific scenes and groups of devices, but they do not load what the user wants immediately, and they do not help to cut down on wait time. Another example of inadequate assistance is during the occurrence of an important family event. Important or noteworthy events may occur when no one is recording audio/video or taking pictures. One participant must act as the recorder or photographer and might be unable to be in the pictures without using a selfie-stick or a tripod and timer.

A yet further, but very common, problem is losing things in the home. Forgetting the last placement of a TV remote control, keys, phones, and other small household items is very common. Existing services (e.g., Tile) for locating such items are very limited or non-existent for some commonly misplaced items. One example shortcoming is that a signaling beacon must be attached to an item to locate it. The signaling beacon needs to be capable of determining its location, for example by using Global Positioning System (GPS). Communication may be via Bluetooth (BT), infrared (IR) light, WiFi, etc. Especially GPS, but also the radio or optical link can require considerable energy, draining batteries quickly. GPS may not be available everywhere in a home, and overall the signaling beacons are costly and inconvenient. Many cellphones include a Find the Phone feature, which allows users to look up the GPS location of their phone or to ring it, if it is on and signed up for the service. However, for many reasons such services and beacons may fail. Further, it is quite possible to lose the devices delivering the location services.

Until now, there has not been a comprehensive solution for the above problems. Embodiments of the invention can solve them all at once.

SUMMARY

There is a need to provide useful, robust and automated, services to a person. Many current services are tied to television (TV) and, therefore, only provided or useful if a user or an object of interest is within view of stationary cameras and/or agents embedded in or stored on a TV. Other current services are tied to a robot only, and may not make use of additional capabilities and capacity offered by available TV sets. Embodiments of the invention overcome this limitation and provide a robot capable of significantly assisting a user.

In a first aspect, an embodiment provides a robot that is capable of interacting with a user. The robot and the user may be in a location such as a house, or an office. The robot comprises a camera, an image recognition processor, a microphone and a loudspeaker, a voice assistant, and a wireless transceiver. The robot can autonomously move around in the location, create a model of the location, and recognize changes in the location. Using the image recognition processor and/or voice assistant, it also recognizes objects of interest, beings (such as the user), and situations. The robot monitors the user. It monitors camera images and recognizes user body language and gesture commands using the image recognition processor. It monitors sounds using the voice assistant, and recognizes voice commands. The robot communicates with the user via the voice assistant and/or the wireless transceiver. It communicates with and controls a TV via the wireless transceiver. It uses the TV display or a handheld device display as a primary display to communicate with the user. It also communicates with other devices via the wireless receiver.

In further embodiments, the robot includes environment sensors, and/or health status sensors. It may also include actuators, such as a video projector. The robot may accept commands from an authorized being, and reject commands from an unauthorized being.

A User Companion

An embodiment of the invention act as a user companion by answering user queries, executing user commands, and issuing reminders. Commands could include making a telephone call, controlling the TV, and generally providing voice assistant functions. Upon the user's command, it may move around the location and stream local images to the TV or primary display.

Further embodiments of the invention monitor the user and determine if the user is well by measuring vital statistics. If and when necessary, they can dispense medication.

Objects of Interest

An embodiment may be taught by the user, through voice commands and local images, that an object is an object of interest. Alternatively, it may autonomously determine that an object is an object of interest by applying deep-learning techniques on local images and local sounds. The embodiment may determine, remember, and report placement of an object of interest. It may also determine if the placement is regular or not. If not, it may alert the user. It may determine a priority for such a user alert and show the alert immediately or at a later time.

Situation Awareness

Embodiments may show situation awareness by moving around the location and monitoring the location for situations. Situations may be user-defined or autonomously defined based on artificial intelligence learning techniques. An embodiment may determine whether situations are regular or not. In a regular situation, it may anticipate one or more commands associated with the regular situation, for example switching a TV to user-preferred content. The embodiment may do so as follows: waiting by an entrance of the location and determining if the user enters; upon determining that the user enters, turning on the TV and forwarding a user profile to the TV; and on the TV, switching on content based on a user preference stored in the user profile. If a situation is not regular, the robot may validate with the user if the situation is desired. If not, it may mitigate the situation, for example by seeking immediate help for the user in an emergency.

Yet further embodiments may capture, categorize, record, and document events as they happen. Such an event could be, for example, a birthday, a party, a child's first steps, a first day of school, a holiday, a change over time, a visit, or a burglary. Embodiments may also categorize and document objects, for example for insurance purposes.

In a second aspect, an embodiment provides a method for a robot to interact with a TV. The method has the following steps. (a) Receiving one or more data streams, wherein the data streams include at least one of video from a camera, audio from a microphone, and data from another sensor configured to provide data to the robot, and wherein a source of the one or more data streams is included in one of the robot, the TV, and an external device. (b) Recording at least one of the one or more data streams. (c) Analyzing at least one of the one or more data streams to recognize at least one of an object of interest, a being, and a situation, and wherein analyzing a video stream includes using an image recognition processor. (d) Selecting one of a recognized object of interest, a recognized being, and a recognized situation, and determining a status of the selected recognized item. (e) Displaying the status on the TV. (f) Inviting a user to command an action based upon the status. (g) Upon receiving a user command, determining if the status must be changed. And (h) upon determining that the status must be changed, changing the status.

A further understanding of the nature and the advantages of particular embodiments disclosed herein may be realized by reference of the remaining portions of the specification and the attached drawings.

BRIEF DESCRIPTION OF THE DRAWINGS

The invention is described with reference to the drawings, in which.

DETAILED DESCRIPTION

There is a need to provide useful, robust and automated, services to a person. Many current services are tied to television (TV) and, therefore, only provided or useful if a user or an object of interest is within view of stationary cameras and/or agents embedded in or stored on a TV. Embodiments of the invention overcome this limitation and provide a method and an apparatus for assisting a robot user, as described in the following.

General

Figure 1:
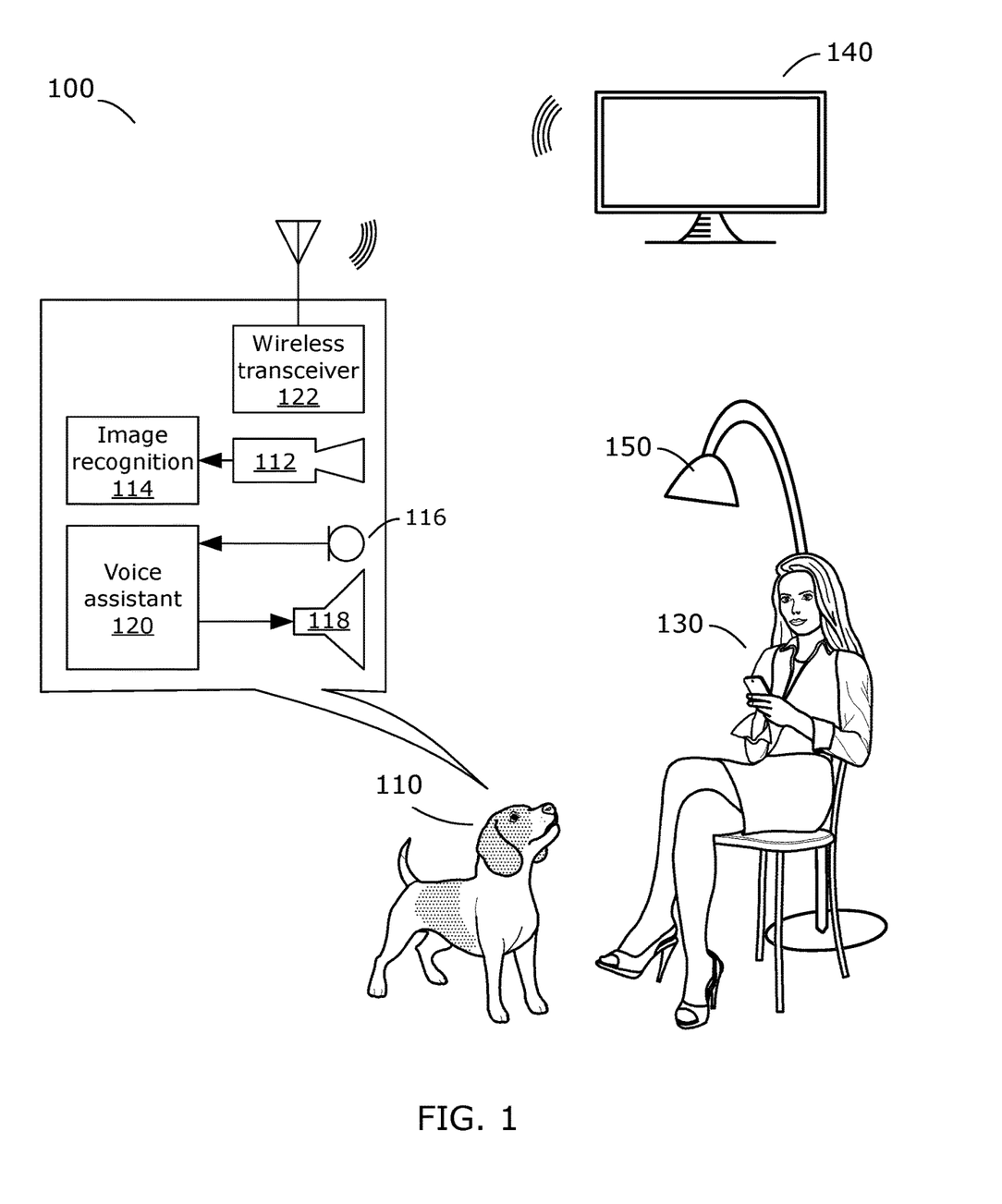
FIG. 1 illustrates a robot capable of interacting with a user in a location according to an embodiment of the invention.

FIG. 1 illustrates a robot 110 capable of interacting with a user 130 in a location 100 according to an embodiment of the invention. Robot 110 comprises camera 112, which is configured to capture local images; image recognition processor 114 coupled to camera 112; microphone 116, which is configured to capture local sounds; loudspeaker 118; voice assistant 120 coupled with microphone 116 and loudspeaker 118; and wireless transceiver 122, which is capable of performing two-way communication. Wireless transceiver 122 may communicate over a radio-frequency (RF) electromagnetic field, or it may communicate optically.

Location 100 may be building, a home, an apartment, an office, a yard, a shop, a store, or generally any location where user 130 may require assistance. Robot 110 may be shaped like a human or like another animal, e.g. Sony's doggy robot aibo, or like a machine that is capable of locomotion, including a drone and a vacuum cleaning robot, or like any other device that may be capable of assisting user 130. Robot 110 may be autonomous, or partially or fully controlled by another device, such as a television (TV 140) that is configured for interacting with robot 110. Both robot 110 and TV 140 may be situated in location 100. Voice assistant 120 may be or include a proprietary system, such as Alexa, Echo, Google Assistant, and Siri, or it may be or include a public-domain system. It may be a general-purpose voice assistant system, or it may be application-specific, or application-oriented. Generally, voice assistant 120 includes an audio recognition processor, an audio production processor, and an artificial intelligence processor. These three processors may be separate, or combined with each other, or distributed over many parallel processors. Wireless transceiver 122 may be configured to use any protocol such as WiFi, Bluetooth, Zigbee, ultra-wideband (UWB), Z-Wave, 6LoWPAN, Thread, 2G, 3G, 4G, 5G, LTE, LTE-M1, narrowband loT (NB-IoT), MiWi, and any other protocol used for RF electromagnetic links, and it may be configured to use an optical link, including infrared IR). Wireless transceiver 122 may be limited to a single protocol or may be configured to support multiple protocols, such as in software-defined radio. Wireless transceiver 122 may consist of a single transceiver, or may include multiple parallel receivers.

Robot 110 is configured to autonomously move around in location 100. It may use camera 112, microphone 116, image recognition processor 114 and/or voice assistant 120 to create a model of location 100 and to recognize and track changes in location 100. Alternatively or additionally, it may use other sensor systems and methods such as sonar, radar, and/or laser scanning (e.g. LIDAR), to create the model and recognize changes therein. Robot 110 further uses image recognition processor 114 to recognize objects of interests and situations. It uses image recognition processor 114 and/or voice assistant 120 to recognize beings, which may include user 130, family members, friends, acquaintances, visitors, coworkers, other humans, pets, and other animals. Robot 110 is further configured to monitor user 130, and is capable of following her or him around in location 100. Monitoring user 130 includes analyzing local images in image recognition processor 114 to recognize, based on deep learning techniques such as used in artificial intelligence, gesture commands and body language. It further includes analyzing local sounds using voice assistant 120 to recognize, based on deep learning techniques, voice commands. Deep learning, in the context of this patent document, means machine learning based on analysis of data, and includes supervised, semi-supervised, and unsupervised learning.

Robot 110 is configured to communicate with the user using the voice assistant 120 and/or wireless transceiver 122. Communication using voice assistant 120 may use loudspeaker 118 or wireless transceiver 122 to reach user 130. Alternatively, robot 110 may use text or an image to communicate with user 130, and transfer the text or the image to user 130 via wireless transceiver 122 and another device, such as TV 140, a handheld device such as a smartphone, or any other device capable of presenting text and/or an image. It is configured to use the TV 140 display or a handheld device display as a primary display to communicate with user 130. It is configured to communicate with and control TV 140 via wireless transceiver 122. It is further configured to communicate with, receive information from, and control other devices via wireless transceiver 122, wherein the other devices may include televisions, cameras, home alarm systems, home appliances, consumer electronics, telephones, lighting, heaters, air conditioners, and any other devices commonly found in a home, office, or other location 100. In the example in FIG. 1, robot 110 communicates with and controls lamp 150, which is part of a lighting system.

Figure 2:
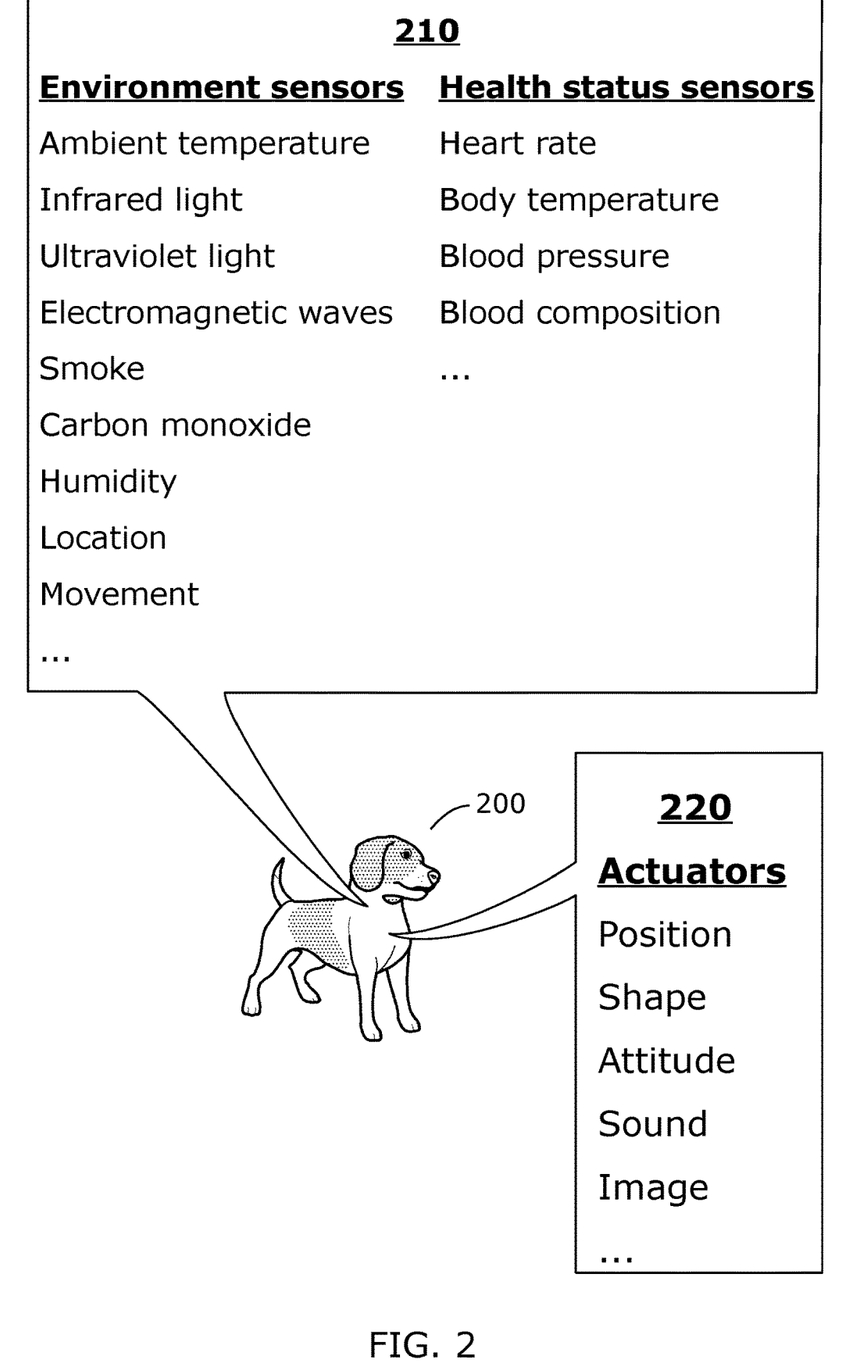
FIG. 2 illustrates a robot with sensors and actuators according to an embodiment of the invention.

FIG. 2 illustrates a robot 200 with sensors 210 and actuators 220 according to an embodiment of the invention. Robot 200 may include environment sensors and/or health status sensors. Environment sensors may sense ambient temperature, infrared light, ultra-violet light, electromagnetic waves of another frequency, pressure, smoke, carbon monoxide, humidity, location, movement, or any other physical quantity or quality related to the environment in which robot 200 may be situated. Health status sensors may sense heart rate, body temperature, blood pressure, blood composition, and any other physical quantity or quality related to the health or physical well-being of user 230 or any other being. Actuators 220 may include motors to control the robot 200 position, shape, and attitude; a loudspeaker; a monitor or display, a video projector; and any other device with which robot 200 may impact itself and/or its environment.

A User Companion

Figure 3:
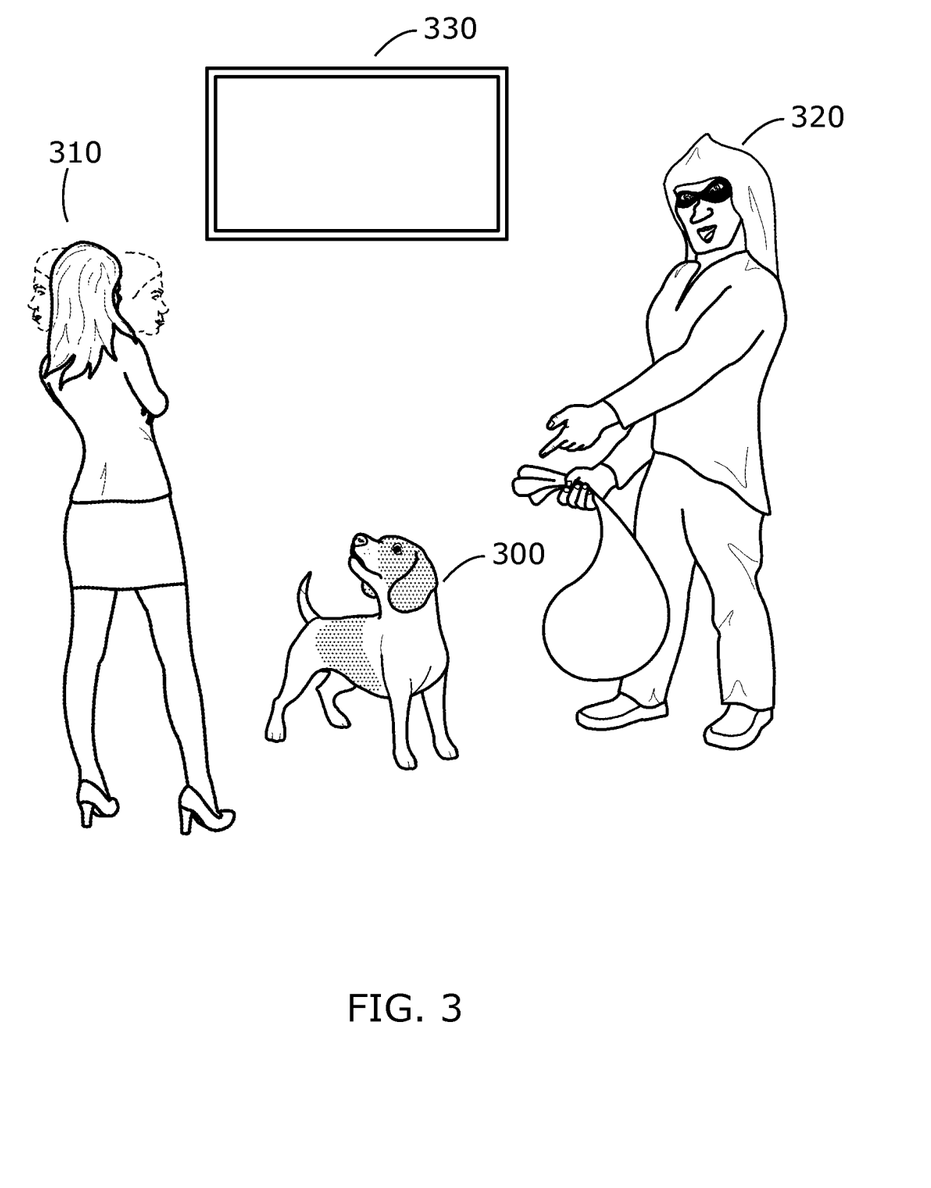
FIG. 3 illustrates a robot accepting commands from an authorized user and rejecting commands from an unauthorized user according to an embodiment of the invention.

FIG. 3 illustrates a robot 300 accepting commands from an authorized user 310 and rejecting commands from an unauthorized user 320 according to an embodiment of the invention. Robot 300 may receive the commands directly, or via another device such as TV 330. In this example situation, unauthorized user 320 demands to know the location of a certain object of interest, whereas authorized user 310 makes a gesture (shaking her head "no") and exhibits body language rejecting the demand. Robot 300 watches the gesture and body language; determines that it is coming from authorized user 310; and ignores conflicting demands coming from unauthorized user 320. In some embodiments, robot 300 ignores unauthorized user 320 even without rejection by authorized user 310. In further embodiments, robot 300 may be configured to execute user commands and answer user queries from authorized user 310, and ignore those from unauthorized user 320. In yet further embodiments, robot 300 may be configured to allow authorized user 310 to temporarily or permanently authorize other users. In even further embodiments, such authorization may be conditional to security and authentication procedures to prevent unauthorized user 320 forcing authorized user 310 to grant authorization, or authorization may be delayed or subject to identification, for example with the use of government issued IDs, fingerprints, and iris scans. Authorization may be partial and limited to groups of commands and queries, such that for example a child may have a lower or different authorization level than an adult, and a visitor may have different authorizations than a family member. Authorization for commands to spend or transfer money may be tied to and limited for specific persons, and may be subject to user authentication.

Figure 4:
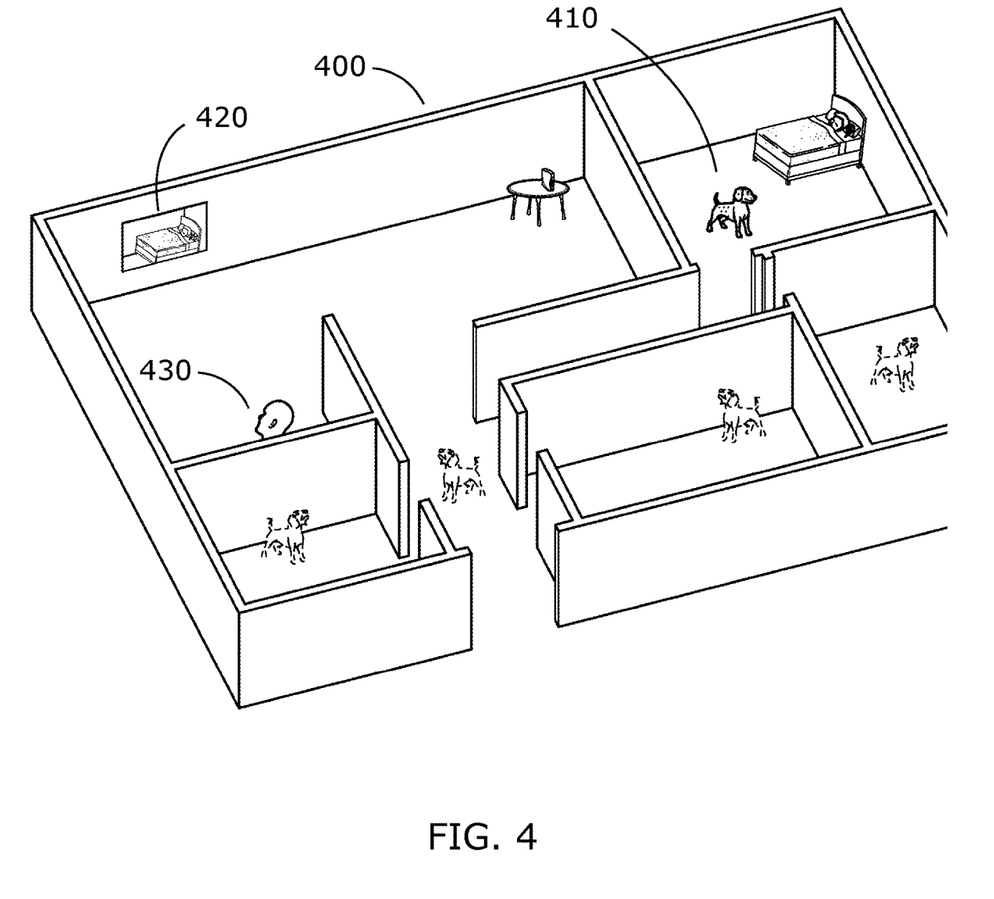
FIG. 4 illustrates a robot moving around a location and streaming local images to a TV.

FIG. 4 illustrates a robot 410 moving around a location 400 and streaming local images to a TV 420. Robot 410 captures the local images with a built-in camera coupled with a wireless transceiver. Autonomously, or upon receiving a command from user 430, robot 410 moves around location 400; captures the local images; forwards the captured local images to the wireless transceiver, and streams the captured local images to TV 420. User 430 may control where robot 410 goes or how robot 410 moves around the location, and which local images it streams to display to user 430.

Figure 5:
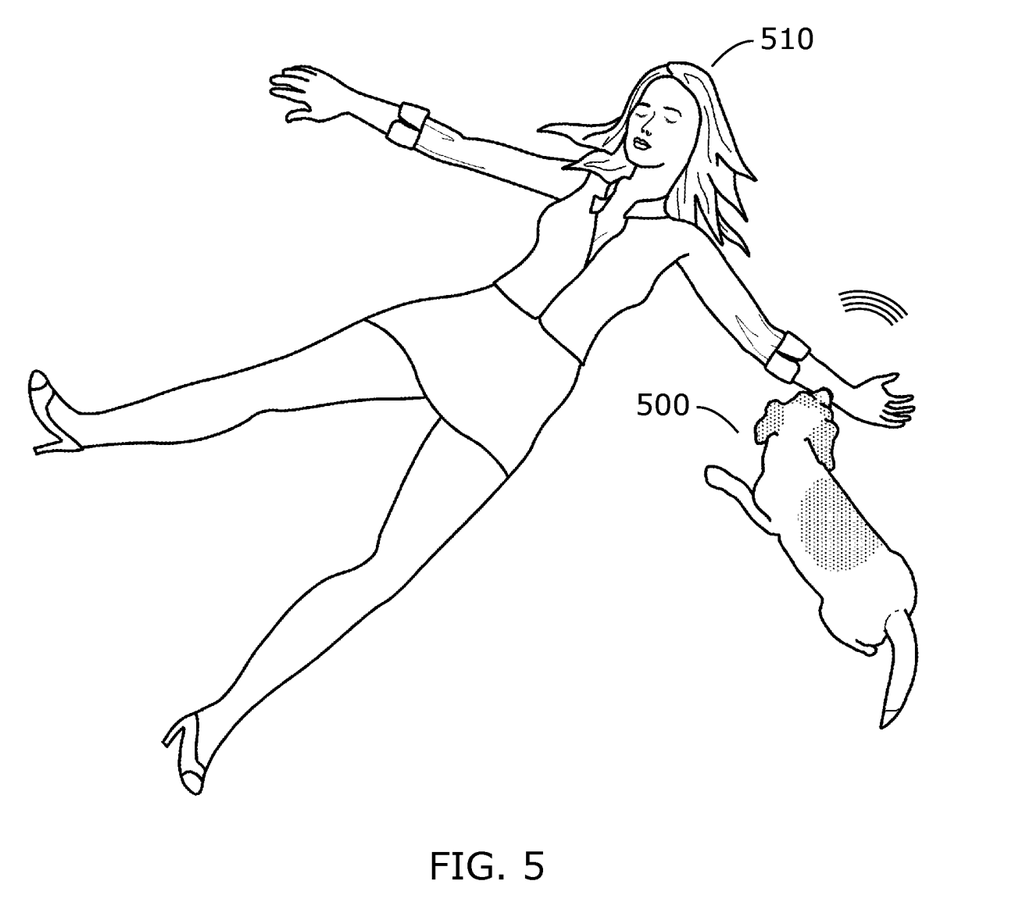
FIG. 5 illustrates a robot that monitors a user by collecting health information according to an embodiment of the invention.

FIG. 5 illustrates a robot 500 that monitors a user 510 by collecting health information according to an embodiment of the invention. Robot 500 may comprise one or more health status sensors, for example to measure heart rate, body temperature, blood pressure, blood composition, or any other quantity or quality related to the health or physical well-being of user 510. For example, robot 500 may comprise a pulse-oximeter to simultaneously measure heart rate and blood oxygenation and a thermometer to determine body temperature. In a further embodiment, it may comprise a blood pressure sensor, a blood glucose monitor, and/or sensors to measure an electro-cardiogram. By measuring user 510's vital statistics regularly, or in cases when user 510 appears to be unresponsive or asks for help, robot 500 monitors her or his well-being, and can assist her or him by remedying a situation, seeking help to remedy the situation, or alerting emergency responders. Monitoring user 510's well-being may include diagnosing a problem based on deep-learning techniques and/or database searches. Some embodiments may establish a line of communication with an emergency responder to allow direct contact between user 510 and the emergency responder. Further embodiments may establish a line of communication with a doctor, which may include audio, video and/or data, to allow the doctor to diagnose a problem remotely. Yet further embodiments may alert user 510 to take medication or may dispense medication to user 510.

Embodiments of robot 500 may use a primary display, such as a built-in display, an image projection, a TV display, a cellphone display, or a handheld device display, to show user 510 communication that may include a reminder, an alert, a text message, an email, an electronic document, a video call, health status information, security information, and/or entertainment.

Objects of Interest

Figure 6:
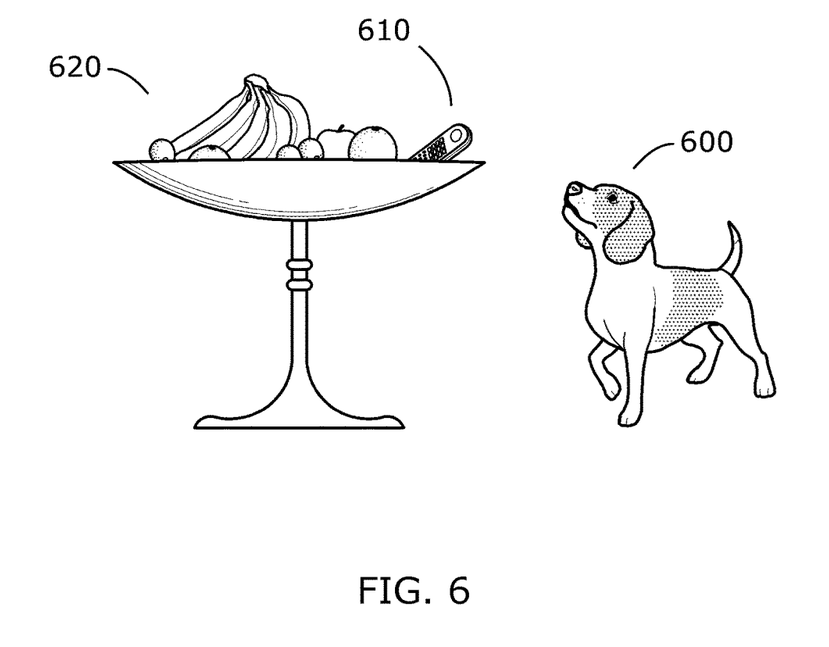
FIG. 6 illustrates a robot noticing an object of interest in an unusual place according to an embodiment of the invention.

FIG. 6 illustrates a robot 600 noticing an object of interest 610 in an unusual place 620 according to an embodiment of the invention. Robot 600 may be configured to be taught by a user, through voice commands and local images, that an object comprises an object of interest. Alternatively or additionally, robot 600 may be configured to determine that an object comprises an object of interest by applying deep-learning techniques on local images and/or local sounds. An embodiment is configured to determine, remember, and report the placement of an object of interest (if placed in an unusual place). To determine the placement, it may use a location sensor, an infrared sensor, sonar, radar, LIDAR (or another laser scanner), and the image recognition processor. It stores the placement in a memory, such as a random-access memory (RAM), a non-volatile memory (NVM), or other non-transitory memory. If the placement is regular, the embodiment does not proactively alert the user. If the placement is unregular, the embodiment may proactively alert the user, or alert the user at a time the object of interest is needed.

In the example of FIG. 6, robot 600 may be moving around the location, and monitoring changes in the location, for example when it finds object of interest 610 (a remote control) in unusual place 620 (a fruit basket). Robot 600 associates object of interest 610 with one or more regular placements and determines that the fruit basket does not constitute a regular placement for the remote control. It remembers the placement by storing it in the non-transitory memory. If configured (e.g., by the user) to proactively report unusual placements, it will issue an alert to the user. Robot 600 may also associate objects of interest with value and/or importance. For example, a wallet or a piece of jewelry may be associated as having higher value or importance than a remote control, or vice versa. The embodiment may determine a priority for alerting the user based on the associated importance and/or the value, and based on the priority it may alert the user proactively or reactively, and it may choose the manner of alerting. For example, it may issue a private alert via a cellphone or handheld device for a high-value object of interest, or a more general alert via a TV screen for a lower-value object of interest. Embodiments may alert the user by showing an image of object of interest 610 along with a timestamp and a marker of the placement. The placement marker could include, for example, a room name or number, a shelf name or number, a height, a distance from a conspicuous other object, or any other information that the user could readily understand identifying the placement. Some embodiments may alert the user by issuing an audio alert. Further embodiments may lead or guide the user to the placement. Yet further embodiments may accept a user command to return object of interest 610 to one of its associated regular placements.

Figure 7:
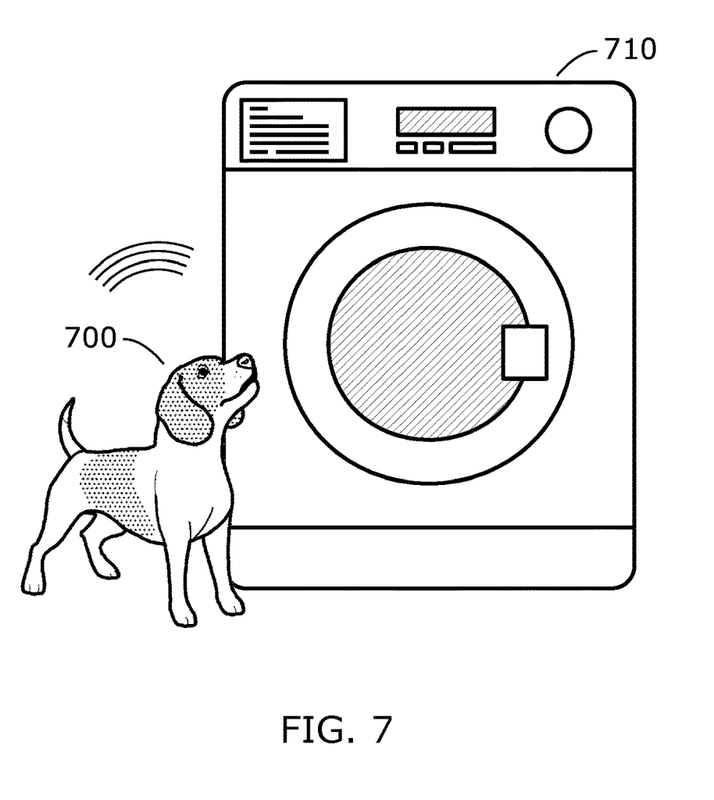
FIG. 7 illustrates a robot monitoring the state of an object of interest according to an embodiment of the invention.

FIG. 7 illustrates a robot 700 monitoring the state of an object of interest 710 according to an embodiment of the invention. In the example of FIG. 7, object of interest 710 is an appliance (a washing machine), and robot 700 determines the state of a laundry job in progress. For example, robot 700 may determine if the laundry job has finished and, if not, how much time is left until completion. Or it may inspect if, after a power outage has occurred, the washing machine has resumed the laundry job that was in progress at the time of the outage. Robot 700 may use local images, as depicted, or may use remote images received from another device, such as a WiFi-connected camera that is installed near the object of interest 710. Similarly, robot 700 may use local or remote sounds to monitor the state of object of interest 710. For example, when a washing machine dries unevenly distributed laundry by spinning it at high speed, it may become mechanically unstable and make a loud noise. Robot 700 may hear and interpret the noise, and alert the user that object of interest 710 has a stability issue and needs attention.

The state of object of interest 710 may be or include a finished task, or a problem that requires user attention. Robot 700 may determine a priority for alerting the user based on the type of task that has finished, or otherwise progressed to a different stage, or on the urgency or type of problem that needs to be solved. It may also be based on knowledge collected by robot 700 about the user's schedule, priority of his or her current activity, or his or her available time now or later. If robot 700 is connected to a TV, for example via a wireless transceiver, it may alert the user via the TV. However, if the user is currently watching content on the TV, then robot 700 may also determine a priority for displaying the content on the TV, for example based on the nature and urgency of the content, and based on the user's personal preferences. An embodiment may compare the priority for alerting the user with the priority for displaying the content, and based on the comparison result display the state of object of interest 710 immediately or at a later time, for example when the content has finished, or when there is a break in the content.

Situation Awareness

In embodiments of the invention, a robot is configured to move around the location, and to monitor the location for situations. Situations are recognized by the use of any sensors present in the robot, including sensors for location, images, and sound, and the use of any processing capability, including that in an image recognition processor and a voice assistant. An embodiment stores situations in non-transitory memory and, as if it were a live being, is most interested in a situation when it has changed. An embodiment can learn situations from moving around and observing the location with all its sensors, and associating observations with its place in the location. It can apply artificial intelligence techniques, including deep learning and data analysis, to define, classify, or categorize situations, and to ease the process of recognizing the situations. Additionally and alternatively, it can learn the situation from the user, or the user can simply define a situation. In further embodiments, a robot determines if a situation is a regular situation or a non-regular situation. In yet further embodiments, a robot determines if a situation is desired (from the user's point of view) or undesired. For example, the robot may communicate the situation to the user by showing and/or describing it, and request the user's feedback on whether the situation is desired. The robot may have been configured to recognize certain situations, such as a fire or flooding, as always undesirable. Or the user may have communicated that a certain situation is always undesirable, such as a receiving junk phone call.

Embodiments of the invention are configured to attempt to mitigate a situation that is not desired. For example, in an emergency situation, a robot may seek immediate help for the user. This may include calling a fire department, emergency medical responders, police, family, relatives and/or neighbors. Or dispensing medicines or fetching a medical device. The robot may establish direct communication between the user and a person who can provide immediate help. Or the robot may search for information, for example on the Internet, that allows the user to mitigate the situation himself or herself.

Figure 8:
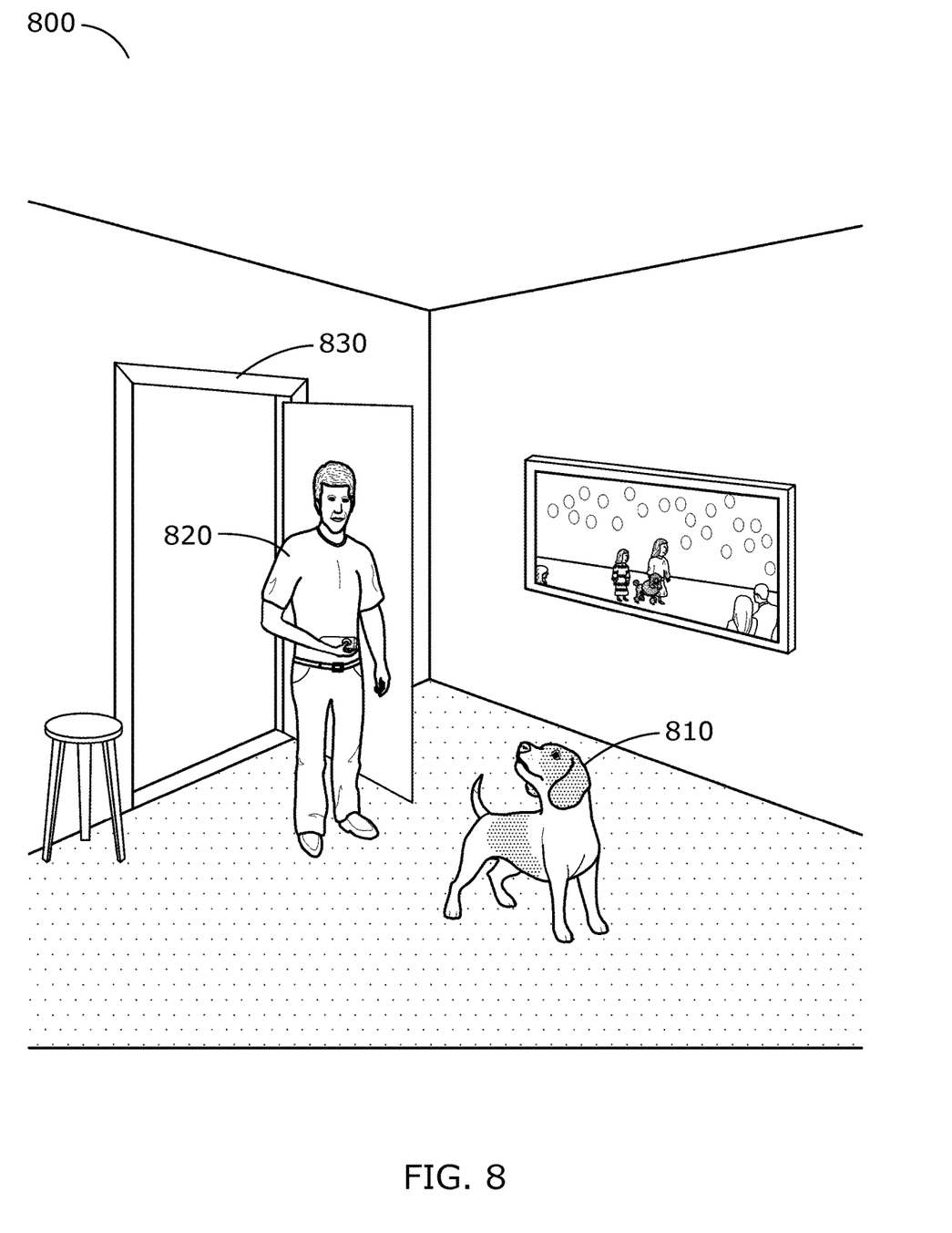
FIG. 8 illustrates a robot recognizing a situation wherein it expects a user command according to an embodiment of the invention.

FIG. 8 illustrates a robot 810 recognizing a situation 800 wherein it expects a user command according to an embodiment of the invention. In this example regular situation, user 820 enters the location via entrance 830. Robot 810 is situated inside the location, and waits for user 820 near entrance 830. When user 820 enters, robot 810 uses its camera and image recognition processor, and/or its microphone and voice assistant, to recognize (identify) user 820. In embodiments, robot 810 may be configured to validate with user 820 if user 820 wants to play preferred entertainment or display preferred information on a device such as a TV or an audio system. In other embodiments, robot 810 may be configured to go ahead without validation, and turn on the device, and any relevant connected components, and play or display preferred entertainment or information based on known user preferences. By following this process, robot 810 ensures that delays are minimal, and the user misses the least information and/or entertainment. Robot 810 effectively anticipates a command, and may execute it even before or without actually receiving the command.

In the example situation 800 depicted in FIG. 8, robot 810 may perform a method with the following steps.

Step (a)—waiting by an entrance of the location, and determining if the user enters.

Step (b)—upon determining that the user enters, turning on the TV and forwarding a user profile to the TV.

Step (c)—on the TV, switching on content based on user preferences stored in the user profile.

Figure 9:
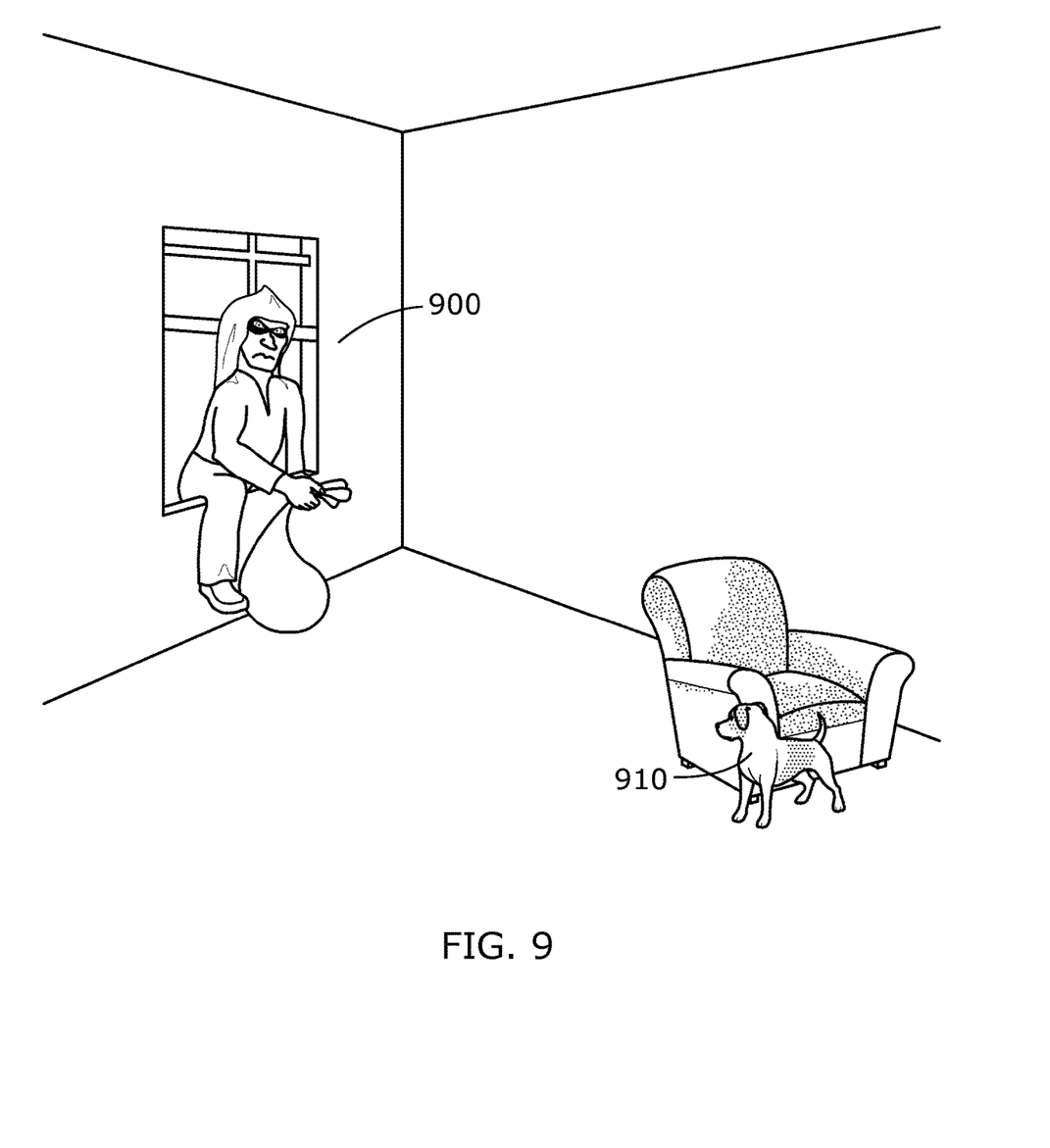
FIG. 9 illustrates a robot capturing, recording and documenting a non-regular situation according to an embodiment of the invention.

FIG. 9 illustrates a robot 910 capturing, recording and documenting a non-regular situation 900 according to an embodiment of the invention. In this context, capturing a situation means sensing video and audio data, as well as any other available sensor data, that are or may be relevant to the situation. Capturing may further include streaming the data to a remote recipient. Recording the situation means storing the data in a non-transitory memory. Categorizing a situation means determining the nature of a situation (e.g., receiving a visit, having a party, a burglary in progress, etc.). Documenting the situation may include determining specific aspects of the situation, recording them, labeling them, and generally preparing them for later review.

Non-regular situations may include positive events such as a party, even a birthday, a child's first steps, a first day of school, a holiday or vacation, or a visit, and negative events such as a burglary. In the example event of FIG. 9, non-regular situation 900 features a burglary in progress. Whereas robot 910 may already have taken or be taking steps to mitigate this undesired situation by calling a security company or the police, it may hide to avoid detection, and it may capture and record non-regular situation 900 as it unfolds. In case of a burglary, chances are high that the perpetrators would try to damage or steal robot 910, and to prevent loss of evidence, the embodiment may stream video, audio, and other relevant data to a remote file server, and may further directly stream this information to the user, and to responders such as the police. An embodiment may categorize and document the situation for later review. For example, it may categorize non-regular situation 900 as a burglary, and it may document the time and duration of the event and all objects of interest that were removed by the burglar(s).

Hopefully, robot 910 has more positive than negative events to capture, categorize, record, and document. In any case, an embodiment may periodically present key events to the user. While such regular presentations may have entertainment value, it also serves to remind the user to take actions planned as a result of some of those key events. Robot 910 may use a primary display device, such as a TV or a handheld device screen, to present the key events. Alternatively, some embodiments may use a built-in projector for the present the key events.

Other Aspects

An embodiment of the invention may communicate with other devices via the wireless transceiver. It may transmit information to and receive information from the other devices, as well as control the other devices. Other devices may be, or include, any of the following: a television, a camera, a home alarm system, components of a home alarm system, a home appliance, consumer electronics, a telephone, a lighting system or component, a heater, an air conditioner, and generally any device that has or may have an electronically controlled function in the location. Information may include a local image, a remote image, a stored image, local sound or audio, remote sound or audio, stored sound or audio, text, sensor information, file and/or folder names, configuration information, version and protocol information, and metadata (i.e., data about data).

An embodiment of the invention may move around the location and categorize and document objects. Categorizing an object means determining the type of object (e.g., furniture, a painting, jewelry, an appliance, a musical instrument, etc.). Documenting the object may include determining specific aspects of the object, recording them, labeling them, and generally preparing them for later review. For example, documenting a painting may include storing an image of the painting, determining its placement and its size, determining from an Internet search if its name and creator are known, asking the user for a name and description of the object, determining its history in the location (has it always had the same placement?), its provenance (Was it bought? When? For how much? Was it given? By whom? Was it inherited? From whom?), and any other information that could later be relevant. Categorizing and documenting objects may have several purposes. For example, it may be used for insurance purposes, investigative purposes after an object has gone missing, or even to prepare for a relocation and to get a quote from a relocation company.

Figure 10:
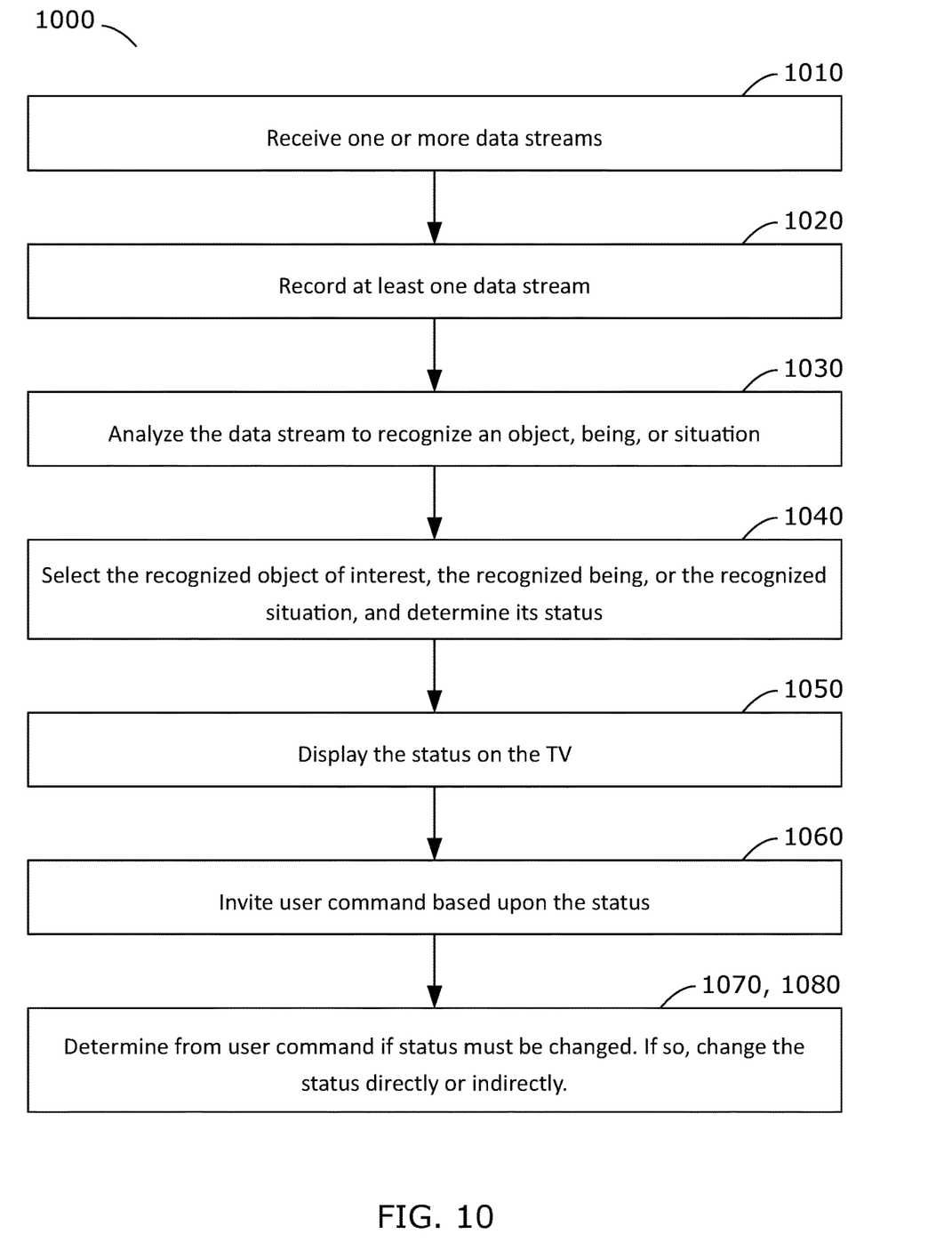
FIG. 10 illustrates a method for a robot to interact with a TV according to an embodiment of the invention.

FIG. 10 illustrates a method 1000 for a robot to interact with a TV according to an embodiment of the invention. The method comprises the following steps.

Step 1010—Receiving one or more data streams. The streams may include one or more of any of the following:

video from a camera, audio from a microphone, and data from another sensor configured to provide data to the robot. A source of the one or more data streams may be included in the robot, the TV, and/or an external device.

Step 1020—Recording at least one of the one or more data streams. Recording includes storing the one or more data stream in a non-transitory memory.

Step 1030—Analyzing at least one of the one or more data streams to recognize an object of interest, a being, or a situation. The embodiment uses an image recognition processor to analyze a video stream or other local image, and/or a voice assistant or audio recognition processor to analyze an audio stream. It may also use the image recognition processor to analyze a laser scan or sonogram. It may further use a processor in the TV as an additional resource for analyzing the at least one of the one or more data streams. Upon recognizing an object of interest, a being, or a situation, it may categorize the object of interest, the being, or the situation, to facilitate further processing. A recognized object may be commonly found in a user household (such as a refrigerator), or it may be particular to the user (such as a tuba). A being may be the user, or a user, family member, a friend, an acquaintance, a visitor, a coworker, another human, a pet, or another animal.

Step 1040—Selecting the recognized object of interest, the recognized being, or the recognized situation, and determining the status of the selected recognized item. The status may depend on the type of the recognized item. For example, an undesired situation may be beginning or ending; a being may be asleep or all wet or very noisy; a refrigerator may have one of its doors standing wide open.

Step 1050—Displaying the status on the TV. Some embodiments may display the status immediately, for example upon determining that the status has high priority or high urgency, or display the status after a delay upon determining that the status has low priority or low urgency. Further embodiments may display the status using the full TV screen, or using picture-in-picture, or closed captions, or another text overlay, or using a general or dedicated alert icon. Yet further embodiments may use an audio alert or voice alert to let the user know that action may be needed.

Step 1060—Inviting the user to issue a command based upon the status. Some embodiments may show or tell the user several options, as in a menu of likely commands. Other embodiments may ask the user an open question, and use a voice assistant to interpret any response by the user.

Step 1070—Upon receiving a user command, determining if the status must be changed. The embodiment receives, interprets, and/or recognizes the command to determine if the command includes a call to action. If it does, the status must be changed.

Step 1080—Upon determining that the status must be changed, changing the status. An embodiment may be able to directly change a status, in which case it sets out to do so. If it is not able to directly change the status, it may be able to find assistance to change the status. For example, if a fire needs to be extinguished and the user commands the embodiment to do so, the embodiment may contact a fire department, or a neighbor to operate a fire extinguisher. Alternatively, while an embodiment may not be able to change a status directly, the TV or another device may be able to change the status, and the embodiment directs the TV or the other device to change the status.

General

Although the description has been described with respect to particular embodiments thereof, these particular embodiments are merely illustrative, and not restrictive. For example, the illustrations show a dog-shaped robot embodying the invention. However, any shape robot meets the spirit and ambit of the invention, and embodiments may work with a single robot or multiple robots, whatever their shape. The illustrations and examples show a single TV. However, embodiments may work with multiple TVs that act in parallel. Methods may be implemented in software, stored in a tangible and non-transitory memory, and executed by a single or by multiple processors. Alternatively, methods may be implemented in hardware, for example custom-designed integrated circuits, or field-programmable gate arrays (FPGAs). The examples distinguish between an image recognition processor and a voice assistant. However, the image recognition processor and the voice assistant may share a processor or set of processors, and only be different in the software executed, or in the software routines being executed.

Any suitable programming language can be used to implement the routines of particular embodiments including C, C++, Java, assembly language, etc. Different programming techniques can be employed such as procedural or object oriented. The routines can execute on a single processing device or multiple processors. Although the steps, operations, or computations may be presented in a specific order, this order may be changed in different particular embodiments. In some particular embodiments, multiple steps shown as sequential in this specification can be performed at the same time.

Particular embodiments may be implemented in a computer-readable non-transitory storage medium for use by or in connection with the instruction execution system, apparatus, system, or device. Particular embodiments can be implemented in the form of control logic in software or hardware or a combination of both. The control logic, when executed by one or more processors, may be operable to perform that which is described in particular embodiments.

Particular embodiments may be implemented by using a programmed general-purpose digital computer, by using application specific integrated circuits, programmable logic devices, field programmable gate arrays, optical, chemical, biological, quantum or nanoengineered systems, components and mechanisms may be used. In general, the functions of particular embodiments can be achieved by any means as is known in the art. Distributed, networked systems, components, and/or circuits can be used. Communication, or transfer, of data may be wired, wireless, or by any other means.

It will also be appreciated that one or more of the elements depicted in the drawings/figures can also be implemented in a more separated or integrated manner, or even removed or rendered as inoperable in certain cases, as is useful in accordance with a particular application. It is also within the spirit and scope to implement a program or code that can be stored in a machine-readable medium to permit a computer to perform any of the methods described above.

A "processor" includes any suitable hardware and/or software system, mechanism or component that processes data, signals or other information. A processor can include a system with a general-purpose central processing unit, multiple processing units, dedicated circuitry for achieving functionality, or other systems. Processing need not be limited to a geographic location, or have temporal limitations. For example, a processor can perform its functions in "real time," "offline," in a "batch mode," etc. Portions of processing can be performed at different times and at different locations, by different (or the same) processing systems. Examples of processing systems can include servers, clients, end user devices, routers, switches, networked storage, etc. A computer may be any processor in communication with a memory. The memory may be any suitable processor-readable storage medium, such as random-access memory (RAM), read-only memory (ROM), magnetic or optical disk, or other non-transitory media suitable for storing instructions for execution by the processor.

As used in the description herein and throughout the claims that follow, "a", "an", and "the" includes plural references unless the context clearly dictates otherwise. Also, as used in the description herein and throughout the claims that follow, the meaning of "in" includes "in" and "on" unless the context clearly dictates otherwise.

Thus, while particular embodiments have been described herein, latitudes of modification, various changes, and substitutions are intended in the foregoing disclosures, and it will be appreciated that in some instances some features of particular embodiments will be employed without a corresponding use of other features without departing from the scope and spirit as set forth. Therefore, many modifications may be made to adapt a particular situation or material to the essential scope and spirit.

We claim:

1. A robot capable of interacting with a user in a location, the robot comprising:
   a camera configured to capture local images;
   an image recognition processor coupled to the camera;
   a microphone configured to capture local sounds and a loudspeaker;
   one or more environment sensors for at least one of ultra-violet light, or humidity;
   a voice assistant coupled to the microphone and the loudspeaker;
   a wireless transceiver capable of performing two-way communication, wherein the wireless transceiver at least one of communicates over a radio-frequency (RF) electromagnetic field and communicates optically; and
   a video projector;
   wherein the robot is configured to:
   autonomously move around in the location;
   create a model of the location and recognize changes in the location;
   recognize an object of interest as being valuable or important to the user based, at least in part, on results from the image recognition processor; determine at least one of: an initial state or one or more regular placements of the object of interest; store the initial state or one or more regular placements, determine at least one of a changed state or a new placement that is unusual compared to the determined one or more regular placements; and based on the determined changed state or determined new placement of the object of interest, communicate an alert to the user;
   recognize beings based on at least one of image recognition results from the image recognition processor and voice recognition, wherein the beings include at least one of the user, a family member, a friend, an acquaintance, a visitor, a coworker, another human, a pet, and another animal;
   recognize the beings based on results from the voice assistant;
   monitor camera images and recognize user body language and gesture commands using the image recognition processor;
   monitor sounds and recognize voice commands using the voice assistant;
   communicate with the user via at least one of the voice assistant and the wireless transceiver;
   communicate with and control a television (TV) via the wireless transceiver;
   using one of a TV display and a handheld device display as a primary display to communicate with the user;
   communicate with, receive information from, and control other devices via the wireless transceiver, wherein the other devices include at least one of a camera, a home alarm system, a home appliance, consumer electronics, a telephone, lighting, a heater, and an air conditioner; and
   accept commands from an authorized being, reject commands from an unauthorized being, and allow the user to at least temporarily authorize another being.

2. The robot of claim 1, further configured to answer user queries using the voice assistant and execute user commands.

3. The robot of claim 2, wherein a user command includes at least one of making a telephone call, controlling the TV, and providing a voice assistant function.

4. The robot of claim 2, configured to move around the location as a response to a user command, and to stream local images to the TV.

5. The robot of claim 1, configured to follow the user in the location using at least one of a camera, a microphone, and another sensor and configured to determine if the user is well.

6. The robot of claim 1, further comprising one or more health status sensors, wherein a health status sensor includes at least one of a heart rate sensor, a temperature sensor, a blood pressure sensor, and a pulse oximeter; and wherein the robot is configured to determine if the user is well by measuring at least one of a user's heart rate, a user's temperature, and a user's blood pressure.

7. The robot of claim 1, further configured to dispense medication.

8. The robot of claim 1, further configured to issue reminders.

9. The robot of claim 1, wherein communication shown on the primary display includes at least one of a reminder, an alert, a text message, an email, health status information, security information, and entertainment.

10. The robot of claim 1, configured to be taught by the user, through voice commands and local images, that an object comprises the object of interest.

11. The robot of claim 1, configured to determine that an object comprises the object of interest by applying deep-learning techniques on at least one of local images and local sounds.

12. The robot of claim 1, wherein the robot further is configured to determine and remember the one or more regular placements and the new placement of the object of interest using at least one of sonar, radar, LIDAR, and another laser scanner, and wherein remembering is performed using a non-transitory memory.

13. The robot of claim 1, wherein alerting the user comprises showing the user an image with a timestamp and a marker of the placement, and giving the user an audio alert.

14. The robot of claim 1, further comprising leading the user to the new placement.

15. The robot of claim 1, further comprising monitoring of the object of interest using at least one of local images, remote images, and local sounds.

16. The robot of claim 15, wherein the object of interest is an appliance to perform a household task, and wherein the initial state and the changed state indicate a progress of the household task.

17. The robot of claim 16, wherein the changed state includes at least one of a finished task and a problem that requires user attention, and wherein the robot immediately displays the state on a TV if a priority for displaying the state on the TV is determined by the robot to be higher than a priority for displaying a content on the TV, and wherein the robot delays displaying the changed state on the TV if the priority for displaying the changed state on the TV is lower than the priority for displaying the content on the TV.

* * * * *